(12) United States Patent
Baril et al.

(10) Patent No.: US 11,648,046 B2
(45) Date of Patent: May 16, 2023

(54) ELECTROSURGICAL INSTRUMENT FOR CUTTING TISSUE

(71) Applicant: Covidien LP, Mansfield, MA (US)

(72) Inventors: Jacob C. Baril, Norwalk, CT (US); Saumya Banerjee, Hamden, CT (US); Matthew A. Dinino, Newington, CT (US); Roy J. Pilletere, North Haven, CT (US); Justin Thomas, New Haven, CT (US); Ernest A. Addi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 266 days.

(21) Appl. No.: 16/861,845

(22) Filed: Apr. 29, 2020

(65) Prior Publication Data
US 2021/0338307 A1 Nov. 4, 2021

(51) Int. Cl.
*A61B 18/12* (2006.01)
*A61B 18/14* (2006.01)
*A61B 18/00* (2006.01)

(52) U.S. Cl.
CPC .......... *A61B 18/1233* (2013.01); *A61B 18/14* (2013.01); *A61B 2018/00083* (2013.01); *A61B 2018/00601* (2013.01); *A61B 2018/00946* (2013.01); *A61B 2018/144* (2013.01); *A61B 2018/1407* (2013.01); *A61B 2018/1422* (2013.01)

(58) Field of Classification Search
CPC ...... A61B 17/32056; A61B 17/320725; A61B 2018/00601; A61B 18/14; A61B 2018/144; A61B 2018/1407; A61B 2018/1412; A61B 2018/1422
See application file for complete search history.

(56) References Cited

U.S. PATENT DOCUMENTS

| | | |
|---|---|---|
| 2,022,065 A | 11/1935 | Wappler |
| 2,047,535 A | 7/1936 | Wappler |
| 3,516,412 A | 6/1970 | Ackerman |
| 3,886,944 A | 6/1975 | Jamshidi |
| 4,161,950 A | 7/1979 | Doss et al. |
| 4,196,734 A | 4/1980 | Harris |
| 4,198,957 A | 4/1980 | Cage et al. |

(Continued)

*Primary Examiner* — Joseph A Stoklosa
*Assistant Examiner* — Marina Delaney Templeton
(74) *Attorney, Agent, or Firm* — Carter, DeLuca & Farrell LLP

(57) ABSTRACT

An electrode assembly for use with an electrosurgical instrument includes a base portion, a return lead adapted to be electrically coupled to a return terminal of an electrosurgical generator, an electrical insulator supported on a distal portion of the return lead, a tensioning mechanism, and an active lead adapted to be electrically coupled to an active terminal of the electrosurgical generator. The tensioning mechanism includes a slider slidably disposed in the base portion, a rotation rod threadably coupled to the slider, and a spring proximally biasing the slider. The active lead having a first end portion securely fixed to the base portion and a second end portion slidably coupled to the rotation rod of the tensioning mechanism. A portion of the active lead extends around the electrical insulator. Rotation of the rotation rod causes axial displacement of the second end portion of the active lead to tension the active lead about the electrical insulator.

20 Claims, 15 Drawing Sheets

(56) References Cited

U.S. PATENT DOCUMENTS

| | | |
|---|---|---|
| 4,485,810 A | 12/1984 | Beard |
| 4,534,347 A | 8/1985 | Taylor |
| 4,622,966 A | 11/1986 | Beard |
| 4,633,880 A | 1/1987 | Osypka et al. |
| 4,862,890 A | 9/1989 | Stasz et al. |
| 5,013,312 A | 5/1991 | Parins et al. |
| 5,085,659 A | 2/1992 | Rydell |
| 5,192,280 A * | 3/1993 | Parins ............... A61B 18/1485 606/50 |
| 5,224,488 A * | 7/1993 | Neuffer ............. A61B 10/0266 600/564 |
| 5,300,068 A | 4/1994 | Rosar et al. |
| 5,360,428 A | 11/1994 | Hutchinson, Jr. |
| 5,441,499 A | 8/1995 | Fritzsch |
| 5,531,744 A | 7/1996 | Nardella et al. |
| 5,536,267 A | 7/1996 | Edwards et al. |
| 5,599,295 A | 2/1997 | Rosen et al. |
| 5,599,346 A | 2/1997 | Edwards et al. |
| 5,611,798 A | 3/1997 | Eggers |
| 6,027,501 A | 2/2000 | Goble et al. |
| 6,217,528 B1 | 4/2001 | Koblish et al. |
| 6,287,304 B1 * | 9/2001 | Eggers ............... A61B 18/1492 606/50 |
| 6,494,881 B1 | 12/2002 | Bales et al. |
| 6,530,924 B1 | 3/2003 | Ellman et al. |
| 6,533,781 B2 | 3/2003 | Heim et al. |
| 6,752,767 B2 | 6/2004 | Turovskiy et al. |
| 7,033,354 B2 | 4/2006 | Keppel |
| 7,371,234 B2 | 5/2008 | Young |
| 7,399,299 B2 | 7/2008 | Daniel et al. |
| 7,419,488 B2 | 9/2008 | Ciarrocca et al. |
| 7,846,108 B2 | 12/2010 | Turovskiy et al. |
| 7,846,158 B2 | 12/2010 | Podhajsky |
| 8,137,345 B2 | 3/2012 | McNall, III et al. |
| 8,968,301 B2 | 3/2015 | Weber |
| 9,060,765 B2 | 6/2015 | Rencher et al. |
| 9,358,065 B2 | 6/2016 | Ladtkow et al. |
| 9,445,863 B2 | 9/2016 | Batchelor et al. |
| 9,775,665 B2 | 10/2017 | Ellman |
| 9,993,287 B2 | 6/2018 | Sartor et al. |
| 10,045,761 B2 | 8/2018 | Weber |
| 10,376,314 B2 | 8/2019 | van der Weide et al. |
| 10,433,898 B2 | 10/2019 | Borgmeier et al. |
| 10,433,899 B2 | 10/2019 | Borgmeier et al. |
| 10,531,917 B2 | 1/2020 | Johnson et al. |
| 2005/0070895 A1 | 3/2005 | Ryan et al. |
| 2005/0070986 A1 * | 3/2005 | Tockman ............... A61N 1/056 607/122 |
| 2005/0283149 A1 | 12/2005 | Thorne et al. |
| 2006/0064113 A1 * | 3/2006 | Nakao ............ A61B 17/320016 606/113 |
| 2007/0078454 A1 | 4/2007 | McPherson |
| 2007/0118110 A1 | 5/2007 | Girard et al. |
| 2007/0149966 A1 | 6/2007 | Dahla et al. |
| 2007/0179494 A1 | 8/2007 | Faure |
| 2007/0219546 A1 | 9/2007 | Mody et al. |
| 2007/0260240 A1 | 11/2007 | Rusin |
| 2007/0265609 A1 | 11/2007 | Thapliyal et al. |
| 2008/0077129 A1 * | 3/2008 | Van Wyk ............. A61B 18/149 606/46 |
| 2008/0281323 A1 | 11/2008 | Burbank et al. |
| 2009/0306642 A1 | 12/2009 | Vankov |
| 2019/0083172 A1 | 3/2019 | Ladtkow et al. |

* cited by examiner

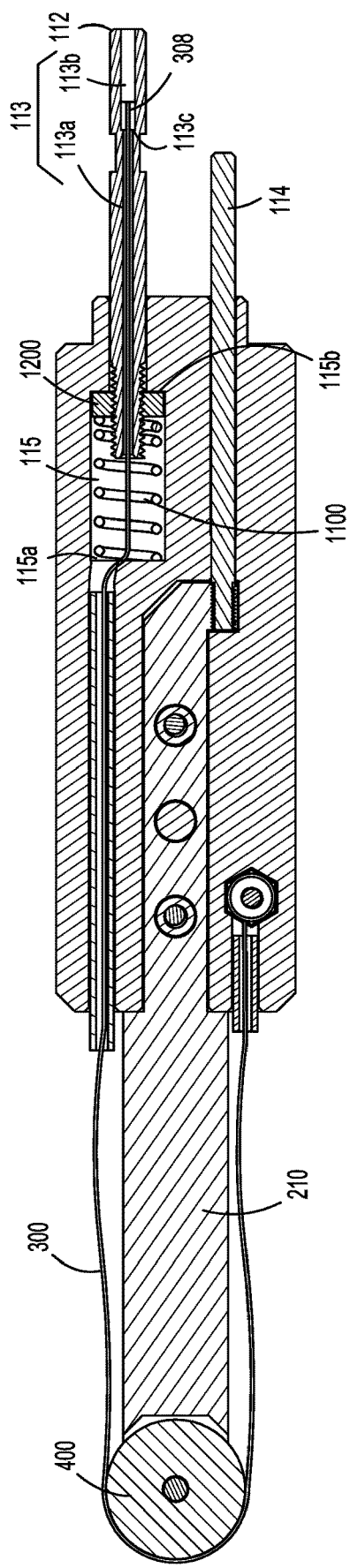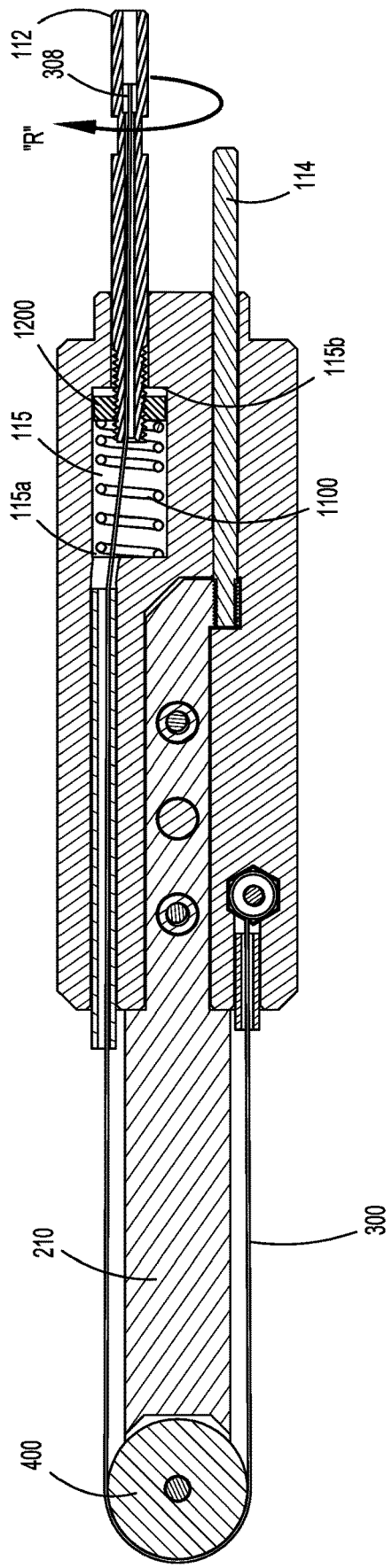
FIG. 5
FIG. 6

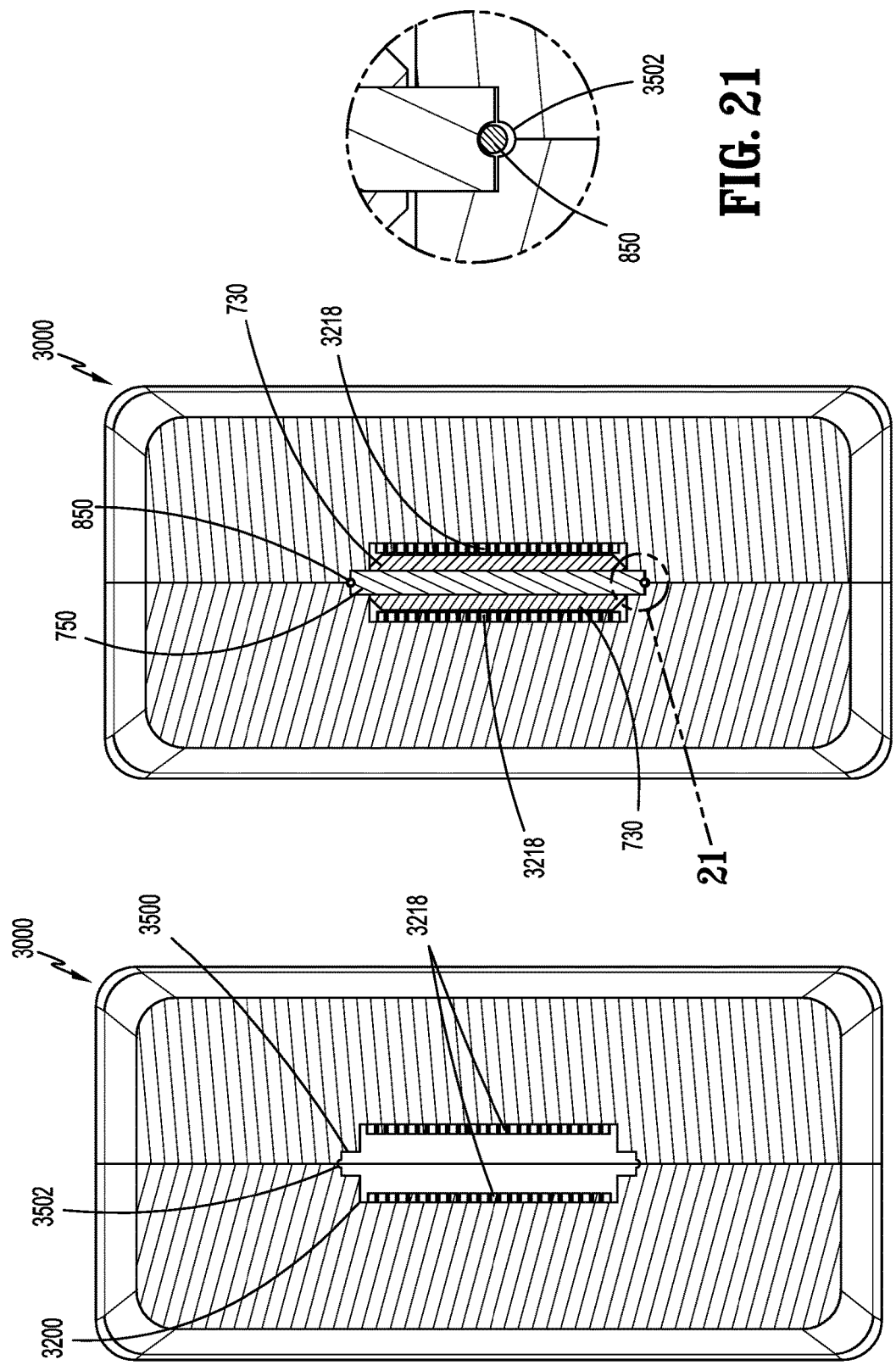

ELECTROSURGICAL INSTRUMENT FOR CUTTING TISSUE

FIELD

The present disclosure relates to surgical instruments and, more particularly, to bipolar electrosurgical instruments for cutting tissue.

BACKGROUND

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical coagulation, electrosurgical sealing, electrosurgical cutting, and/or electrosurgical fulguration or, in some instances, an electrosurgical blend thereof.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a hand switch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow preset control parameters and stay within known modes and power settings and electrosurgical pencils include simple and ergonomically friendly controls that are easily selected to regulate the various modes and power settings Electrosurgical instruments are typically configured such that power output can be adjusted without the surgeon having to turn his or her vision away from the operating site and toward the electrosurgical generator.

SUMMARY

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In accordance with an aspect of the present disclosure, an electrode assembly for use with an electrosurgical instrument includes a base portion, a return lead adapted to be electrically coupled to a return terminal of an electrosurgical generator, an electrical insulator supported on a distal portion of the return lead, a tensioning mechanism, and an active lead adapted to be electrically coupled to an active terminal of the electrosurgical generator. The tensioning mechanism includes a slider slidably disposed in the base portion, a rotation rod threadably coupled to the slider, and a spring proximally biasing the slider. The active lead having a first end portion securely fixed to the base portion and a second end portion slidably coupled to the rotation rod of the tensioning mechanism. A portion of the active lead extends around the electrical insulator. Rotation of the rotation rod causes axial displacement of the second end portion of the active lead to tension the active lead about the electrical insulator.

In an aspect of the present disclosure, the rotation rod of the tensioning mechanism may define a lumen configured to receive the active lead.

In another aspect of the present disclosure, the lumen may have a first portion having a first diameter and a second portion distal of the first portion and having a second diameter smaller than the first diameter.

In yet another aspect of the present disclosure, the second end portion of the active lead may have a stop slidably received in the first portion. The stop may have a diameter larger than the second diameter of the second portion of the lumen.

In still another aspect of the present disclosure, the electrical insulator may define a groove on a peripheral portion thereof. The active lead may be configured to be received within the groove.

In still yet another aspect of the present disclosure, the base portion may include first and second insulation tubes electrically insulating the respective first and second end portions of the active lead.

In another aspect of the present disclosure, the active lead may be a wire.

In yet another aspect of the present disclosure, the electrical insulator may be rotatably supported on the return lead.

In still yet another aspect of the present disclosure, electrical insulator may be formed of ceramic.

In still yet another aspect of the present disclosure, a portion of the active lead and the return lead may define a gap therebetween.

In accordance with another aspect of the present disclosure, an electrode assembly for use with an electrosurgical instrument includes a base portion, an electrical insulator coupled to the base portion, an active lead adapted to be electrically coupled to a first electrical potential of an electrosurgical generator, a return lead adapted to be electrically coupled to a second electrical potential of the electrosurgical generator, and a tensioning mechanism including a slider configured to support a portion of the active lead, and a rotation rod threadably engaging the slider such that rotation of the rotation rod causes axial displacement of the slider to tension the active lead about the electrical insulator. The active lead defines a loop.

In an aspect of the present disclosure, the slider may include an engaging portion defining a threaded bore configured to threadably engage the rotation rod, and a hook portion axially-aligned with the electrical insulator.

In another aspect of the present disclosure, the hook portion may have an arcuate profile configured to engage the active lead.

In still another aspect of the present disclosure, the active lead may be a wire forming the loop.

In an aspect of the present disclosure, the rotation rod may include a portion having a polygonal cross-section.

In another aspect of the present disclosure, the base portion may further include a removable clip configured to engage the polygonal cross-section of the rotation rod to inhibit rotation of the rotation rod.

In accordance with yet another aspect of the present disclosure, a tool system for use with an electrosurgical device for cutting tissue includes a tool assembly and a cleaning assembly. The tool assembly includes a base portion and a tool portion. The tool portion includes an electrical insulator supported on the base portion, a return lead adapted to be electrically coupled to a return terminal, and an active lead adapted to be electrically coupled to an active terminal. The return lead is supported on the electrical insulator. The active lead is supported on a peripheral portion of the electrical insulator. Upon activation, electrosurgical energy is transmitted from the active lead through tissue to the return lead to cut tissue in contact with the active lead. The cleaning assembly includes a body defining a slot configured to receive the tool portion of the tool assembly. The body includes bristles to remove debris from the tool portion.

In an aspect of the present disclosure, the body of the cleaning assembly may further define lateral grooves on respective lateral sides of the slot. The lateral grooves may be configured to receive the electrical insulator laterally outwards of the return lead.

In another aspect of the present disclosure, the lateral grooves may include respective arcuate portions configured to receive the active lead supported on the peripheral portion of the electrical insulator.

In still another aspect of the present disclosure, the body of the cleaning assembly may include first and second housing halves detachably coupled to each other.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

FIGS. 5-7 are cross-sectional views of the tool assembly of FIG. 1, illustrating use of a tensioning mechanism of the tool assembly;

FIG. 19 is a cross-sectional view of the cleaning assembly of FIG. 15 taken along section line 19-19 of FIG. 15;

FIG. 20 is a cross-sectional view of the cleaning system of FIG. 18 taken along section line 20-20 of FIG. 18; and FIG. 21 is an enlarged cross-sectional view of the indicated area of detail of FIG. 20.

DETAILED DESCRIPTION

Figure 1:
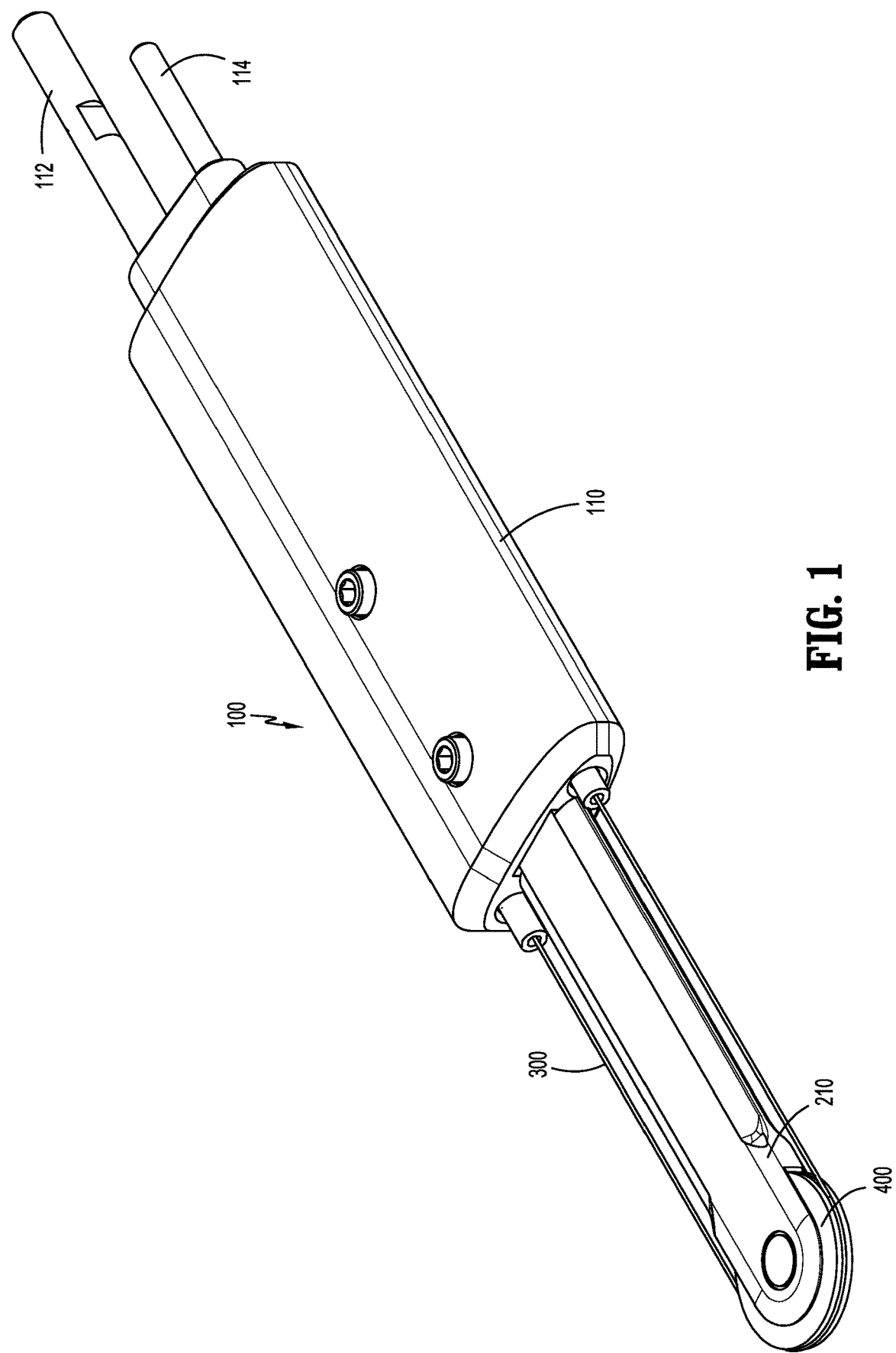
FIG. 1 is a perspective view of a tool assembly for use with an electrosurgical device in accordance with an aspect of the present disclosure.

Turning now to FIG. 1, a tool assembly or end effector assembly for use with an electrosurgical device in accordance with an aspect of the present disclosure is generally shown as an end effector assembly 100 adapted to be electrically coupled to an electrosurgical energy source such as, e.g., a generator (not shown), to provide bipolar radio-frequency (RF) power output. The electrosurgical energy source may include electronic circuitry configured to generate radio frequency energy specifically suited for various electrosurgical modes and/or procedures. The electrosurgical energy source may include one or more converting devices for converting from DC to AC or vice versa. The electrosurgical device may be configured to transmit any suitable electric current (e.g., AC and/or DC) at any suitable frequency. For a detailed discussion of the construction and operation of exemplary electrosurgical devices and electrosurgical energy sources, reference may be made to U.S. Patent Publication Nos. 2013/0267947 and 2013/0255063; and U.S. Pat. Nos. 7,156,844 and 5,766,167, the entire contents of each of which are incorporated by reference herein.

Figure 2:
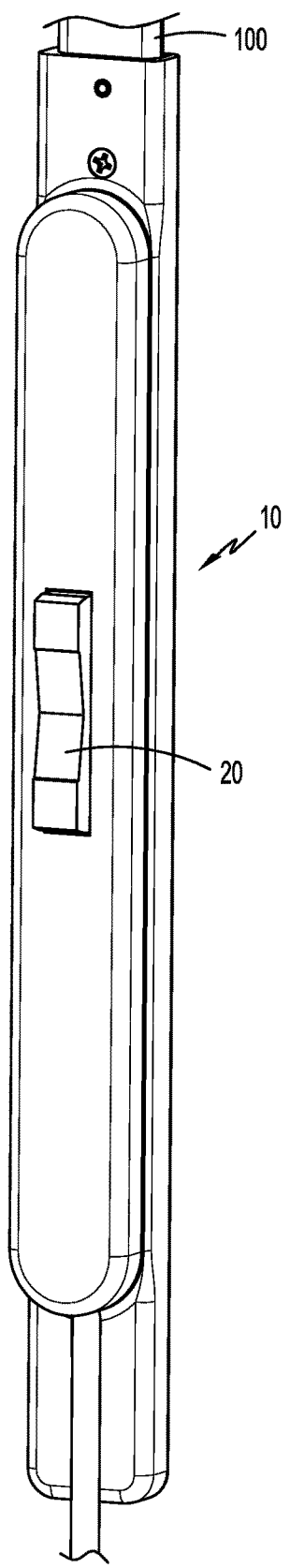
FIG. 2 is a perspective view of a handle of the electrosurgical device for use with the tool assembly of FIG. 1.
Figure 3:
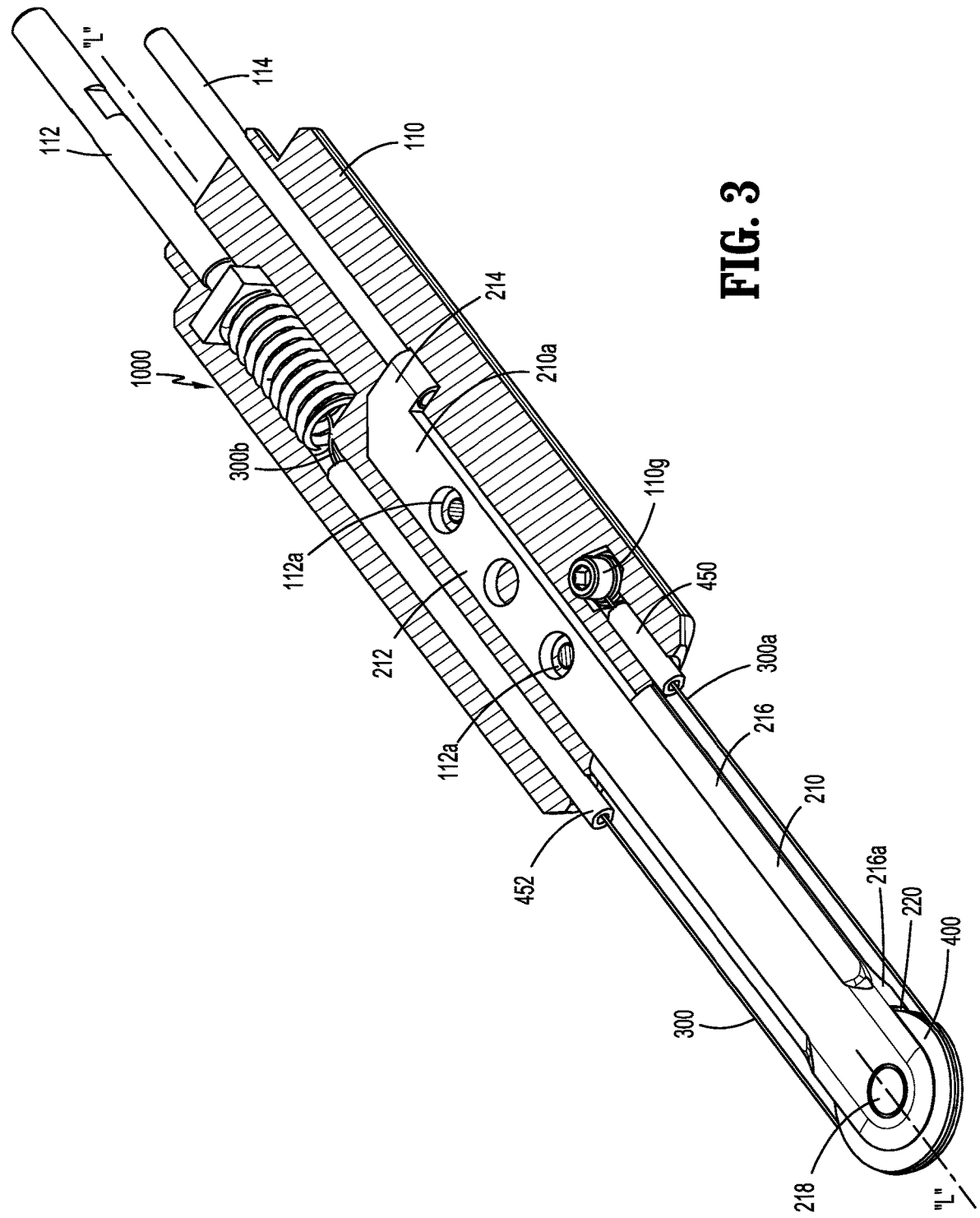
FIG. 3 is a perspective view of the tool assembly of FIG. 1 with a part of the base portion removed.

With reference to FIGS. 1-3, the end effector assembly 100 includes a tensioning mechanism 1000 configured to ensure a desired tension in an active lead 300 throughout the use of the end effector assembly 100, as will be discussed. The end effector assembly 100 is coupled (releasably or integrally) to a body portion 10 (FIG. 2), e.g., a handpiece, of an electrosurgical device. For example, the body portion 10 of the electrosurgical device may include a switch 20 to control electrical communication between the electrosurgical energy source and the active lead 300 for selectively activating the active lead 300 to cut tissue. The end effector assembly 100 may be configured to connect to a robotic arm of a robotic surgical system to enable manipulation and control thereof.

The end effector assembly 100 includes a base portion 110 formed of or coated with an electrically-insulative material, a return lead 210 electrically coupled to an electrosurgical energy source (e.g., via a return terminal), the active lead 300 electrically coupled to the electrosurgical energy source (e.g., via an active terminal), an electrical insulator 400 rotatably supported on the return lead 210, and a tensioning mechanism 1000. In addition, the base portion 110 includes a supply line 112, e.g., an electrical contact pin, electrically coupling the active lead 300 to the active terminal of the electrosurgical energy source, and a return line 114, e.g., an electrical contact pin, electrically coupling the return lead 210 to the return terminal of the electrosurgical energy source. The return lead 210 serves as an electrical return for electrosurgical energy (e.g., electric current) conducted through the active lead 300.

Figure 4:
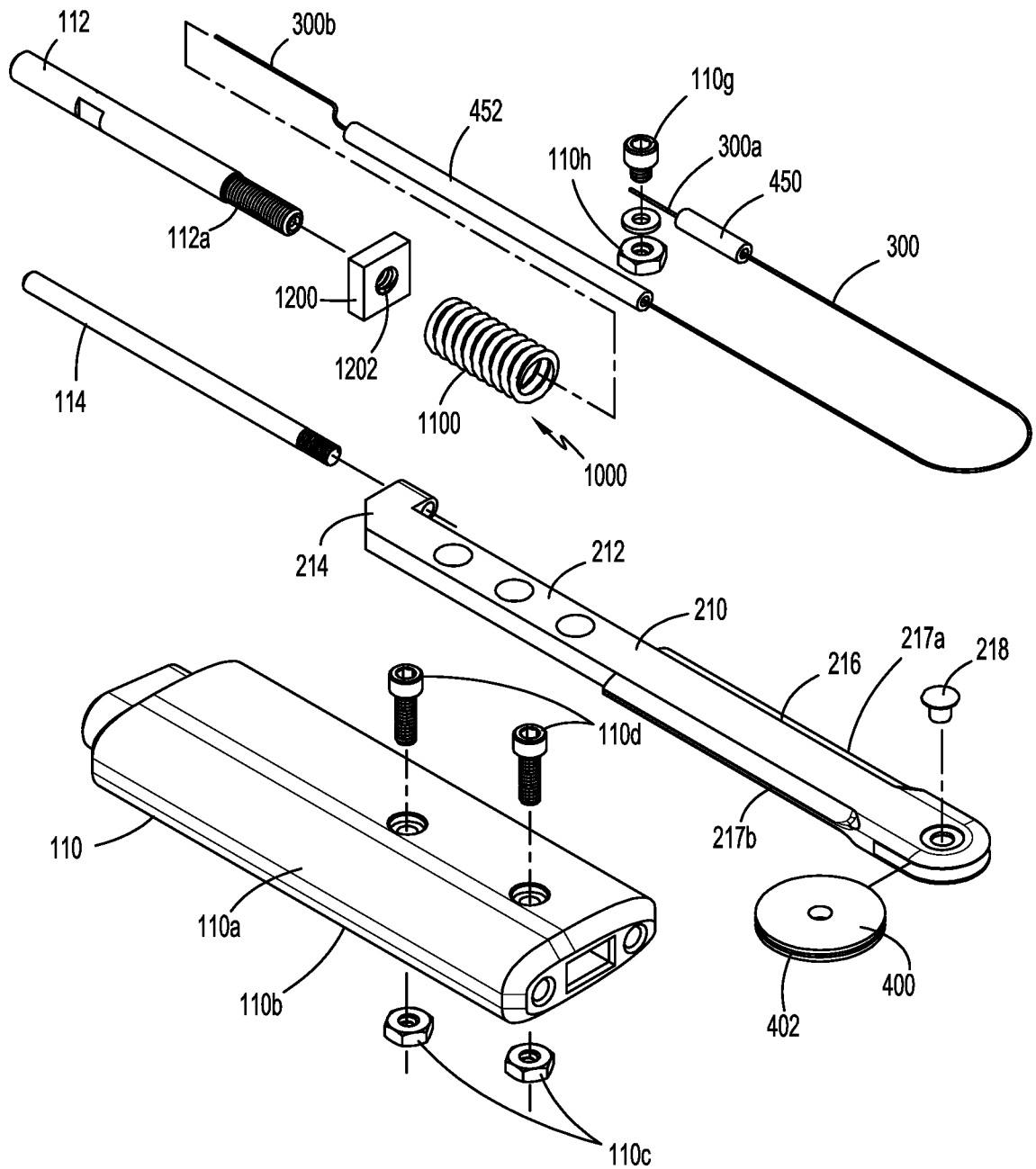
FIG. 4 is an exploded perspective view of the tool assembly of FIG. 1 with parts separated.

With particular reference to FIGS. 3 and 4, the base portion 110 includes first and second housing halves 110a, 110b that are secured to each other by nuts and bolts 110c, 110d. The first and second housing halves 110a, 110b define respective cavities configured to securely receive at least a portion of the proximal portion 210a of the return lead 210. The return lead 210 includes an elongated portion 212, an offset portion 214 offset from a longitudinal axis "L-L" defined by the elongate portion 212, and an extension portion 216 extending distally from the base portion 110. The base portion 110 securely supports the return lead 210 thereon. The cavities of the first and second housing halves 110a, 110b are shaped complementary to the shape of the portion of the return lead 210 disposed therein to inhibit axial displacement of the return lead 210 relative to the base portion 110. Further, the elongated portion 212 of the return lead 210 defines bores 112a configured to receive respective bolts 110d therethrough in order to further secure and inhibit axial displacement of the return lead 210 relative to the base portion 110.

The extension portion 216 of the return lead 210 extends distally from the base portion 110. In particular, the extension portion 216 includes a distal portion 216a rotatably supporting the electrical insulator 400 about a pin 218. In particular, the distal portion 216a defines an arcuate recess 220 having a shape complementary to the shape of the electrical insulator 400 such that a peripheral portion of the electrical insulator 400 and distal portion 216a of the extension portion 216 define a gap therebetween.

The elongated portion 212, the offset portion 214, and the extension portion 216 of the return lead 210 may be formed as a single construct. For example, the elongated portion 212, the offset portion 214, and the extension portion 216 of the return lead 210 may be monolithically formed of stainless steel. Any portion of the return lead 210 may serve as an electrical return for electrosurgical energy (e.g., electric current) conducted through the active lead 300. A large surface area of the return lead 210 compared to the small surface area of the active lead 300 may provide a desirable ratio of return surface area to cutting surface area for high efficiency in cutting tissue.

With continued reference to FIGS. 3 and 4, the electrical insulator 400 is in a form of a wheel or a pulley that is rotatably supported on the return lead 210. The electrical insulator 400 defines a circumferential groove 402 configured to receive at least a portion of the active lead 300 therein. The electrical insulator 400 may be formed of a ceramic material due to its hardness and inherent ability to withstand high temperature fluctuations. Alternatively, the electrical insulator 400 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAD, Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

With continued reference to FIGS. 3 and 4, the active lead 300 may be in a form of a wire formed of, e.g., tungsten. A first end portion 300a of the active lead 300 is secured to the base portion 110 by a bolt 110g and a nut 110h. In addition, the first end portion 300a is received through a first insulation tube 450 configured to electrically insulate the active lead 300 from the return lead 210. In particular, at least a portion of the first insulation tube 450 extends distally from the base portion 110. A second end portion 300b of the active lead 300 is operatively coupled to the tensioning mechanism 1000 disposed in the base portion 110. The second end portion 300b is received through a second insulation tube 452. The second insulation tube 452 extends distally from the base portion 110 and electrically insulates the second end portion 300b from the return lead 210. A portion of the active lead 300 extends around the electrical insulator 400. In particular, the portion of the active lead 300 is supported in the circumferential groove 402 defined in the electrical insulator 400. The active lead 300 may be configured to provide, e.g., a line, contact with tissue to minimize the surface contacting tissue. The active lead 300 and the return lead 210 define a gap therebetween to facilitate cutting of tissue by the active lead 300.

With reference to FIGS. 4 and 5, the tensioning mechanism 1000 is operatively supported in the base portion 110. Rapid heat cycling may cause the active lead 300 to stretch and lose tension, which in turn, may disengage the active lead 300 from the electrical insulator 400. The tensioning mechanism 1000 provides selective tightening of the active lead 300 by the clinician as needed. The tensioning mechanism 1000 includes a compression spring 1100 and a slider 1200 that are slidably received in a cavity 115 defined in the base portion 110. The compression spring 1100 ensures that the active lead 300 remains taut throughout use. The compression spring 1100 is interposed between a distal support wall 115a of the base portion 110 and the slider 1200.

The slider 1200 defines a threaded bore 1202 configured to threadably engage a threaded portion 112a of the supply line 112. In particular, the supply line 112 defines a lumen 113 therethrough. The second end portion 300b of the active lead 300 extends through the compression spring 1100 and the lumen 113 of the supply line 112 threadably received through the slider 1200. The lumen 113 includes a first portion 113a and a second portion 113b proximal of the first portion 113a. The second portion 113b has a diameter larger than a diameter of the first portion 113a. The second end portion 300b of the active lead 300 includes a stop 308 having a diameter dimensioned to be received in the second portion 113b of the lumen 113, but larger than the diameter of the first portion 113a of the lumen 113. The stop 308 may include, e.g., a ferrule or a crimped hypotube, to inhibit passage through the first portion 113a of the lumen 113.

Figure 7:
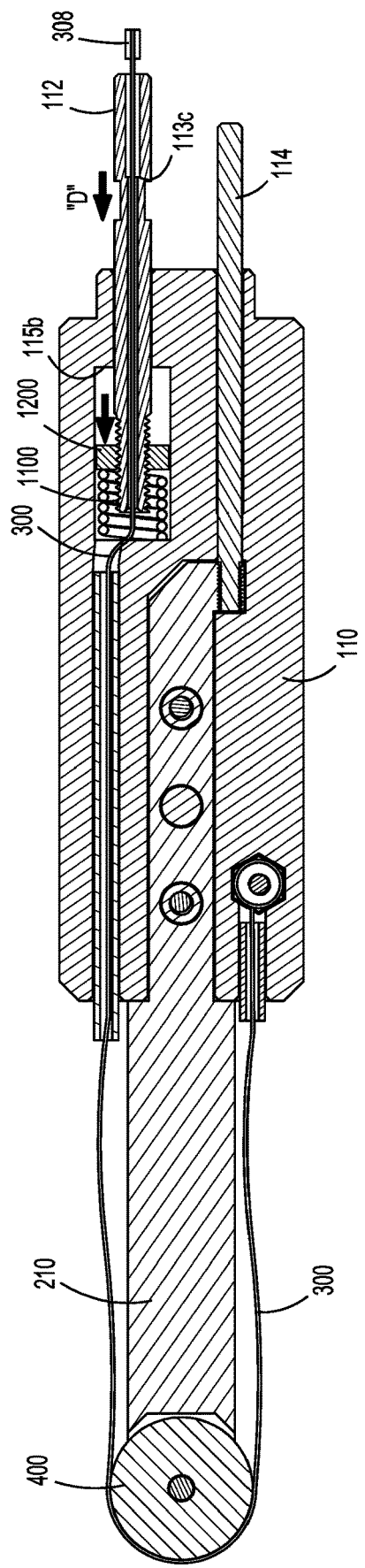

With particular reference to FIG. 5, when the active lead 300 has slack, the slider 1200 of the tensioning mechanism 1000 engages a proximal supporting wall 115b of the base portion 110. At this time, the stop 308 of the active lead 300 is disposed in the second portion 113b of the lumen 113 of the supply line 112. With reference to FIG. 6, rotation of the supply line 112 in the direction of, e.g., an arrow R, causes displacement of the supply line 112 in a proximal direction relative to the slider 1200, which, in turn, enables the clinician to increase tension in the active lead 300. At this time, the slider 1200 is displaced from the proximal supporting wall 115b and the compression spring 1100 is compressed. With reference now to FIG. 7, the supply line 112 may be displaced in the direction of an arrow D to remove tension in the active lead 300. The supply line 112 may be displaced in the direction of the arrow D by pushing the supply line 112 in the direction of arrow D or may be rotated in a direction opposite of the arrow R (FIG. 6). At this time, the stop 308 may be spaced apart from the transition portion 113c of the lumen 113 or displaced proximally from the lumen 113 of the supply pin 112.

The return lead 210 may contact tissue at approximately the same time as the active lead 300, and thus allowing it to cut or otherwise treat tissue. The return lead 210 returns the electrosurgical energy to the electrosurgical energy source. In this manner, the electrosurgical energy applied via the active lead 300 across tissue severs tissue (or simply electrosurgically treats tissue) in contact with the active lead 300.

In use, a clinician may adjust the tension of the active lead 300 by rotating the supply line 112 in the direction of the arrow "R" (FIG. 6). The clinician may position the end effector assembly 100 operatively coupled to an electrosurgical device adjacent a target tissue. When the active lead 300 engages tissue to be cut, the return lead 210 may be pushed against the surrounding tissue. In order to cut tissue from a surgical site, the electrosurgical device is activated by actuating the switch 20 of the body portion 10 (see FIG. 2) to supply electrosurgical energy to the active lead 300. Activation of the electrosurgical device draws the electrosurgical energy from the electrosurgical energy source to the active lead 300. For example, the return lead 210 contacts tissue at approximately the same time as the active lead 300, and thus performing a cut in tissue. Any portion of the return lead 210 may serve as an electrical return for electrosurgical energy (e.g., electric current) conducted through the active lead 300. The return lead 210 returns the electrosurgical energy to the electrosurgical energy source via the return terminal of the electrosurgical energy source. Under such a configuration, the electrosurgical energy applied via the active lead 300 across tissue severs the tissue. This process may be repeated as necessary. After tissue is removed, the clinician may coagulate and/or cauterize the tissue to control bleeding, if necessary.

Figure 8:
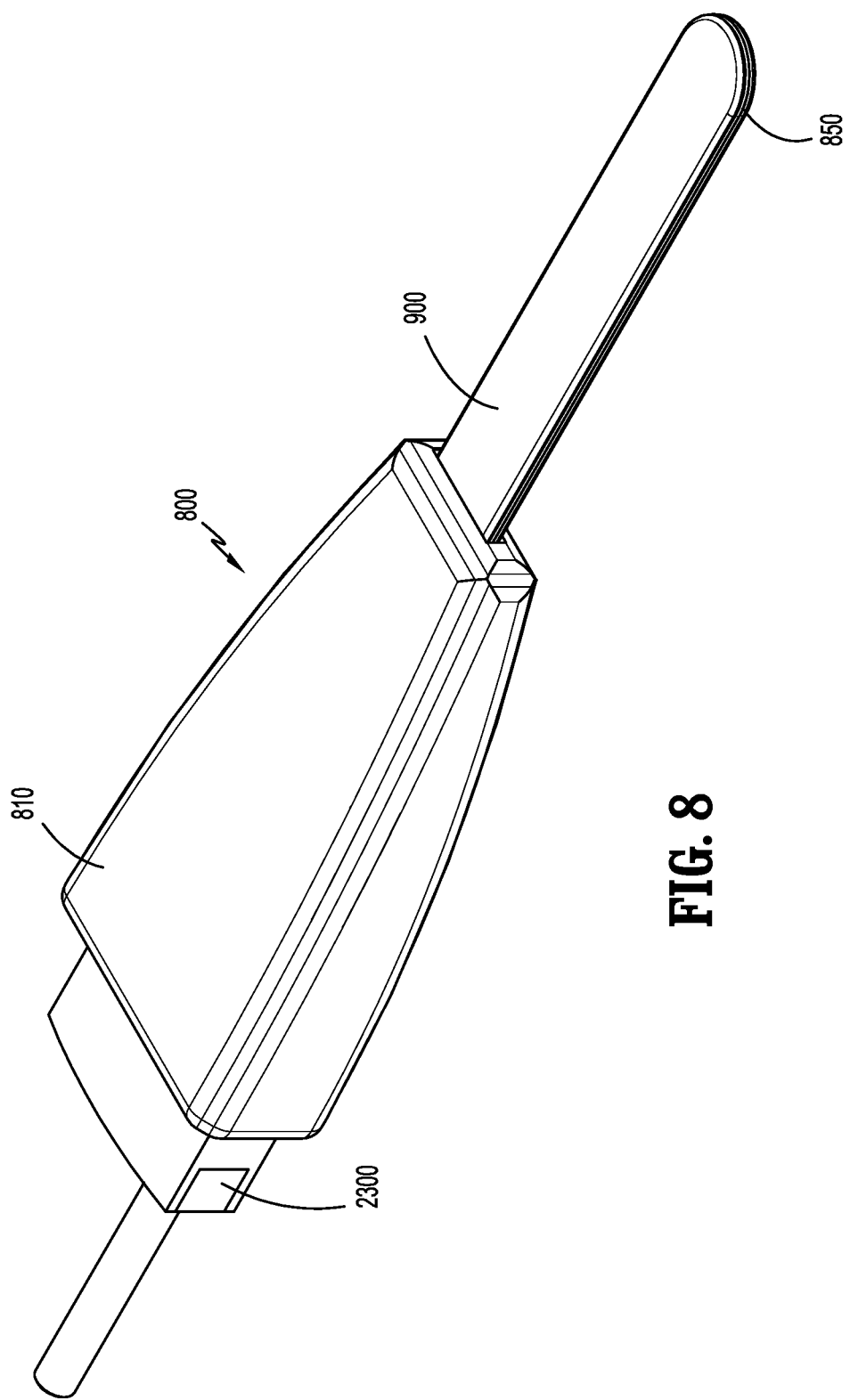
FIG. 8 is a perspective view of a tool assembly for use with an electrosurgical device in accordance with another aspect of the present disclosure.
Figure 9:
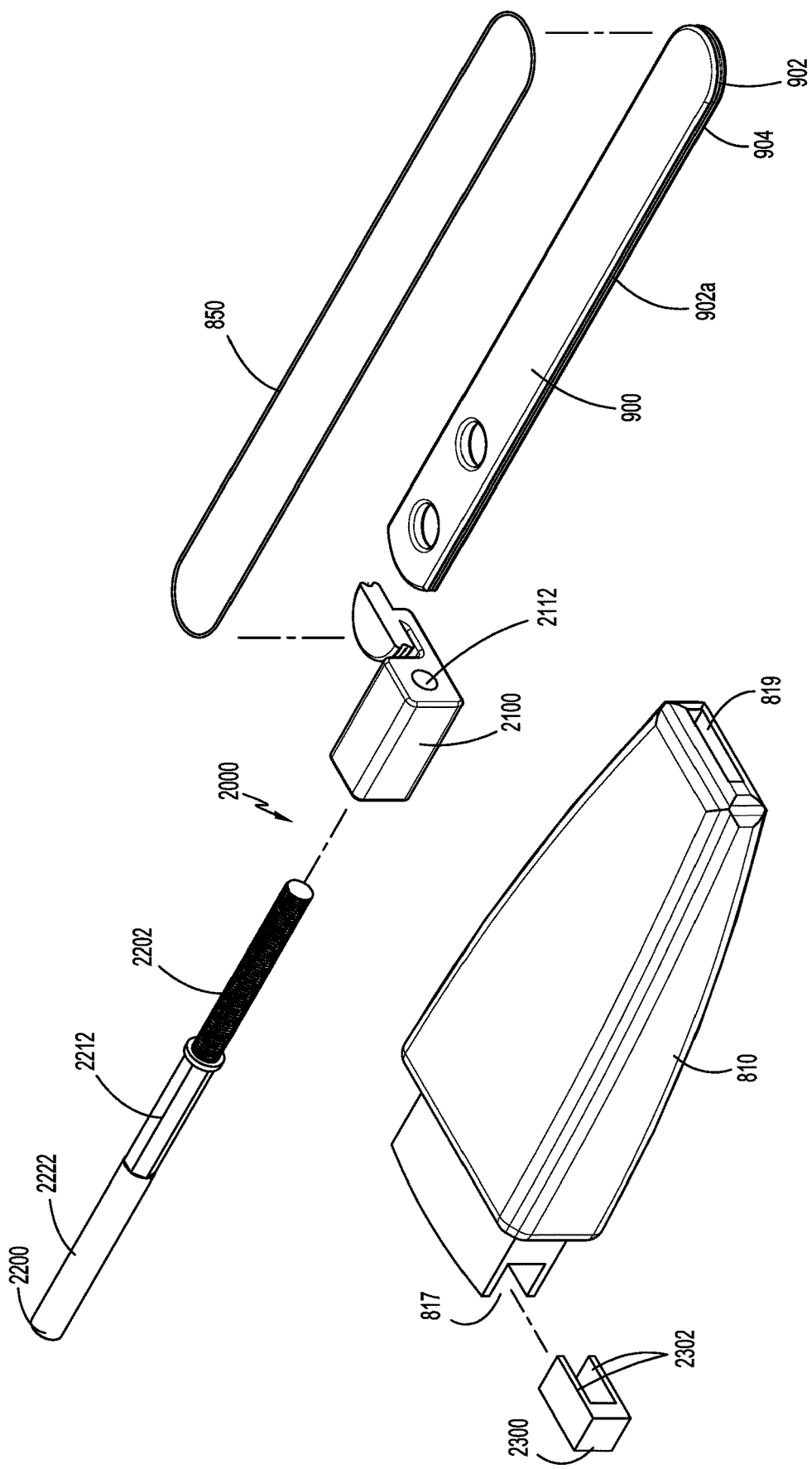
FIG. 9 is an exploded perspective view of the tool assembly of FIG. 8 with parts separated.

With reference now to FIGS. 8 and 9, there is provided an end effector assembly 800 for use with an electrosurgical device including a tensioning mechanism 2000 in accordance with another aspect of the present disclosure. In the interest of brevity, portions of the end effector assembly 800 substantially similar to the portion of the end effector assembly 100 will not be described herein to avoid obscuring the present disclosure in unnecessary detail.

The end effector assembly 800 is adapted to be coupled (releasably or integrally) to the body portion 10 (reference FIG. 2), e.g., a handpiece, of an electrosurgical device to cut tissue. For example, the body portion of the electrosurgical device may include a switch to control electrical communication between the electrosurgical energy source and an active lead 850 for selectively activating the active lead 850 to cut tissue. The end effector assembly 800 includes the active lead 850 electrically coupled to the electrosurgical energy source (e.g., via an active terminal), an electrical insulator 900 supporting the active lead 850 on a peripheral portion thereof, a return lead (not shown) electrically coupled to the electrosurgical energy source (e.g., via a return terminal) disposed on the electrical insulator 900 in a superposed relation (see, e.g., FIG. 15), a base portion 810 supporting the electrical insulator 900, and a tensioning mechanism 2000 configured to selectively adjust the tension of the active lead 850. The return lead serves as an electrical return for electrosurgical energy (e.g., electric current) conducted through the active lead 850. The active lead 850 may be formed of a conductive material such, e.g., tungsten. In contrast to the end effector assembly 100, the active lead 850 is formed of a wire defining a continuous loop as will be described below.

Figure 10:
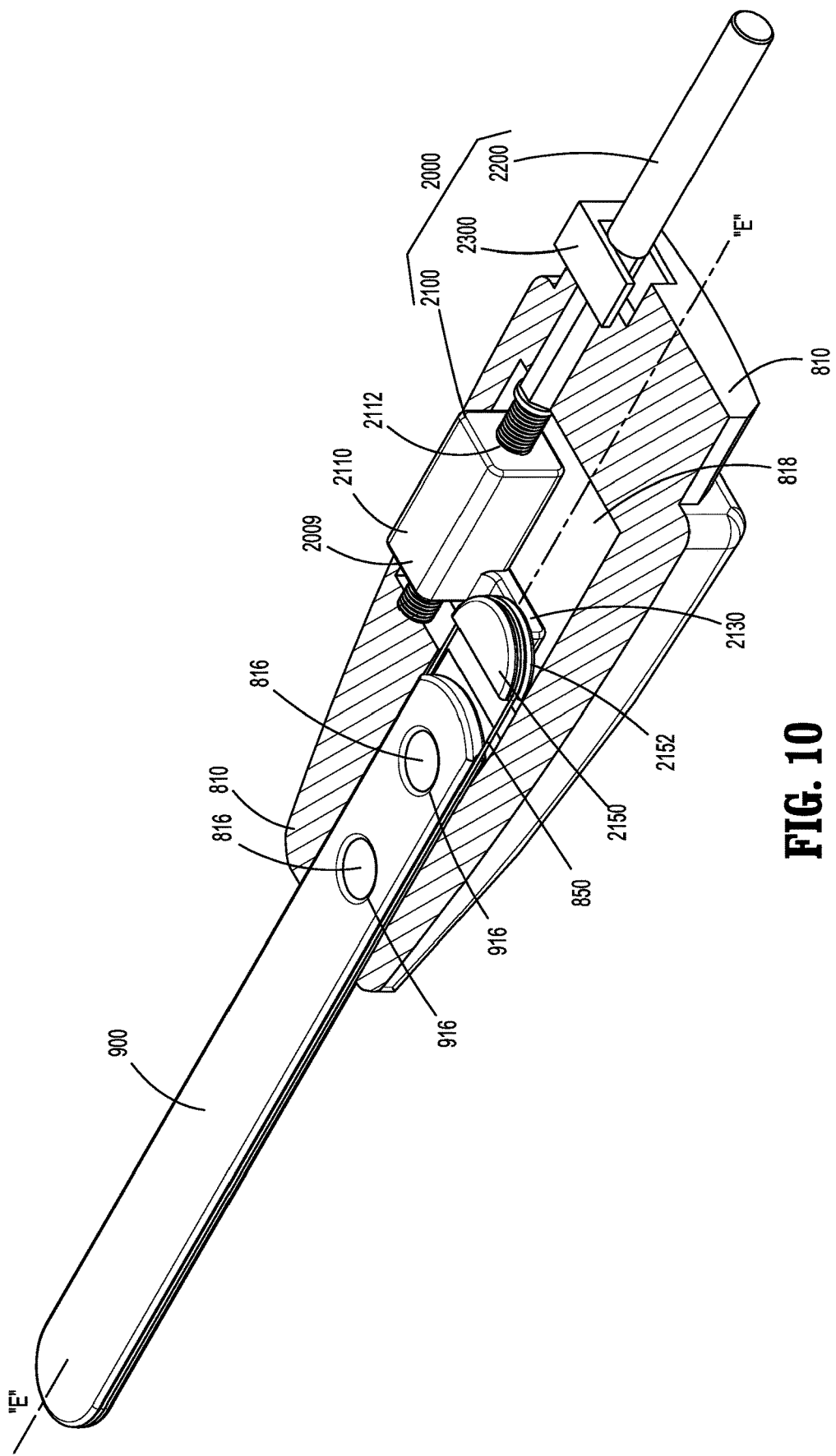
FIG. 10 is a perspective view of the tool assembly of FIG. 8 with a portion of the base portion removed.

With reference to FIG. 10, the base portion 810 may be formed of or coated with an electrically-insulative material. The base portion 810 includes protrusions 816 configured to be received in respective bores 916 defined in the electrical insulator 900 to secure the electrical insulator 900 to the base portion 810. For example, the protrusions 816 of the base portion 810 may be secured with the base portion 810 by, e.g., friction fit, ultrasonic welding, etc. The electrical insulator 900 extends through a slot 819 (FIG. 9) of the base portion 810 and supports the active lead 850 on a peripheral portion 902 (FIG. 9) of the electrical insulator 900. In particular, the peripheral portion 902 defines a groove 902a configured to receive the active lead 850 therein. For example, the electrical insulator 900 may be formed of a ceramic material due to its hardness and inherent ability to withstand high temperature fluctuations. Alternatively, the electrical insulator 900 may be made from a material having a high Comparative Tracking Index (CTI) having a value in the range of about 300 to about 600 volts. Examples of high CTI materials include nylons and syndiotactic polystyrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

With continued reference to FIG. 10, the tensioning mechanism 2000 includes a slider 2100, a rotation rod 2200, and a locking clip 2300. The slider 2100 is slidably received in the cavity 818 of the base portion 810 for axial displacement. The slider 2100 includes an engaging portion 2110 defining a threaded bore 2112 (FIG. 9) threadably engaging the rotation rod 2200, a lateral wing 2130 extending laterally from the engaging portion 2110, and a hook portion 2150 supported on the lateral wing 2130. The engaging portion 2110 includes opposed engaging surfaces 2009 (only one shown in FIG. 10) slidably engaging the base portion 810 for axial displacement thereof. The opposed engaging surfaces 2009 include respective planar surfaces that inhibit rotation of the slider 2100 about the rotation rod 2200 when the slider 2100 threadably engages the rotation rod 2200. The hook portion 2150 is axially aligned with the electrical insulator 900. The hook portion 2150 is formed as a single construct with the engaging portion 2110 such that axial movement of the engaging portion 2110 causes axial displacement of the hook portion 2150 along a longitudinal axis "E-E" defined by the electrical insulator 900. For example, the hook portion 2150 and the engaging portion 2110 may be monolithically formed. The hook portion 2150 has an arcuate profile and defines a groove 2152 configured to receive a portion of the active lead 850 therein. Under such a configuration, rotation of the rotation rod 2200 causes axial displacement of the slider 2100 along the longitudinal axis "E-E" of the electrical insulator 900, which, in turn, displaces the hook portion 2150 relative to the electrical insulator 900 that is fixed to the base portion 810. In this manner, tension in the active lead 850 defining a loop is selectively adjustable by the clinician through rotation of the rotation rod 2200.

With brief reference back to FIG. 9, the base portion 810 defines a cutout 817 configured to receive the locking clip 2300 therein. The locking clip 2300 includes a substantially U-shaped profile. In particular, the locking clip 2300 includes opposing engaging surfaces 2302 configured to engage the rotation rod 2200 to inhibit rotation of the rotation rod 2200. The rotation rod 2200 includes a threaded portion 2202 configured to threadably engage the threaded bore 2112 of the slider 2100, a locking portion 2212 proximal of the threaded portion 2202, and a rotatable portion 2222 proximal of the locking portion 2212 and configured to be rotated by the clinician. In particular, the locking portion 2212 has a non-circular cross-section such as, e.g., a polygonal cross-section. Under such a configuration, when the locking clip 2300 is inserted into the cutout 817 of the base portion 810, the engaging surfaces 2302 of the locking clip 2300 engage polygonal surfaces of the locking portion 2212 to inhibit rotation of the rotation rod 2200. In this manner, the clinician may utilize the locking clip 2300 to maintain the desired tension of the active lead 850 after the desired tension is obtained in the active lead 850.

Figure 11:
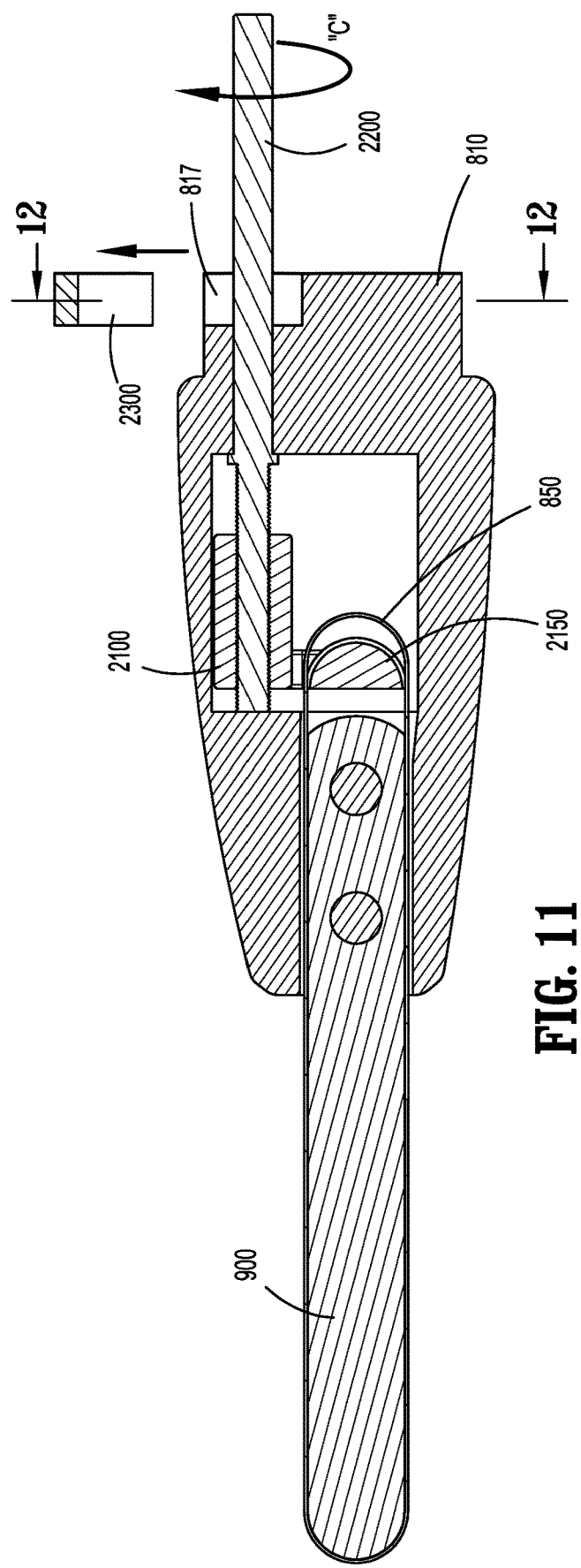
FIG. 11 is a cross-sectional view of the tool assembly of FIG. 8.
Figure 12:
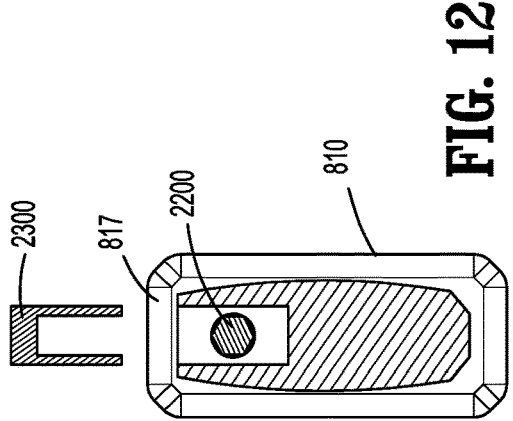
FIG. 12 is a cross-sectional view of the tool assembly of FIG. 8 taken along section line 12-12 of FIG. 11.

With reference to FIGS. 11 and 12, when the slider 2100 is displaced proximally such that the hook portion 2150 and the electrical insulator 900 define a relatively small gap therebetween, the active lead 850 has slack such that, e.g., the active lead 850 is spaced apart from the groove 2152 (FIG. 10) of the hook portion 2150. In order to provide desired tension in the active lead 850, the locking clip 2300 is removed from the cutout 817 of the base portion 810 and the rotation rod 2200 is rotated in the direction of an arrow "C".

Figure 13:
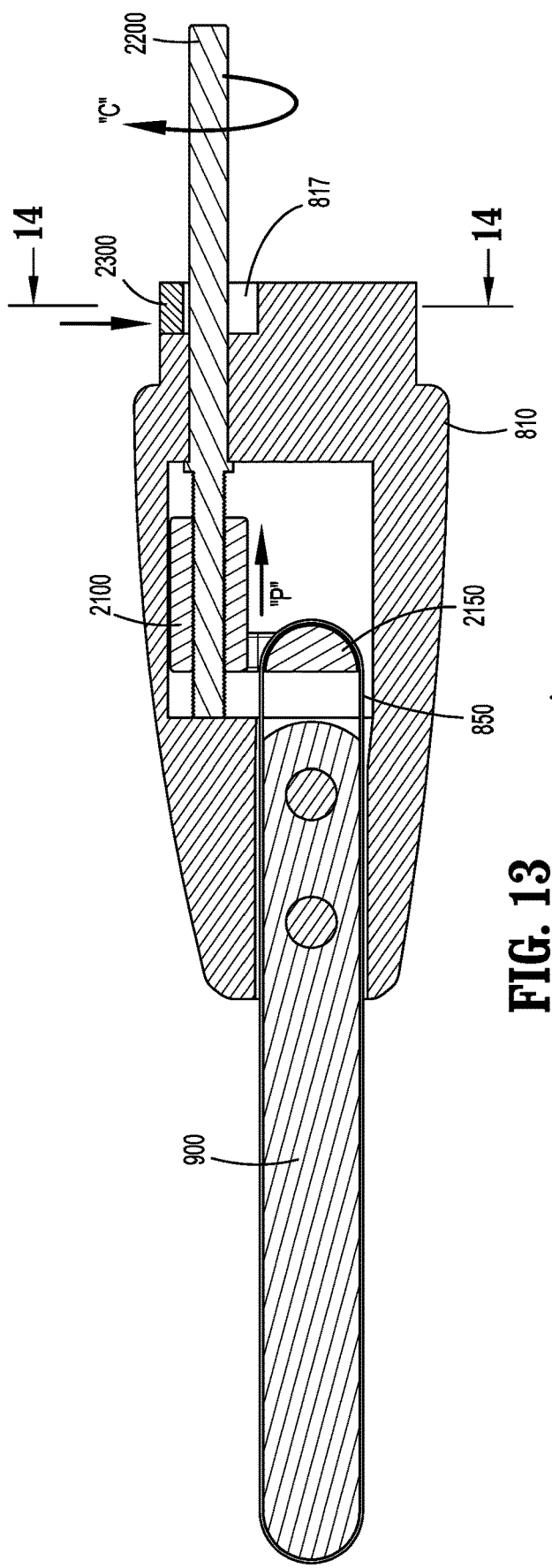
FIG. 13 is a cross-sectional view of the tool assembly of FIG. 8, illustrating use of a tensioning mechanism of the tool assembly.
Figure 14:
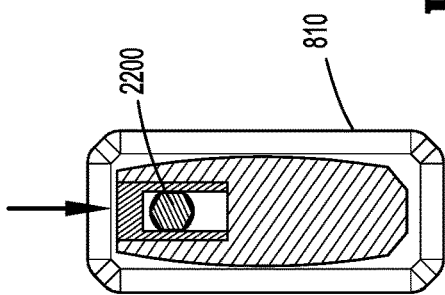
FIG. 14 is a cross-sectional view of the tool assembly of FIG. 13 taken along section line 14-14 of FIG. 13.

With reference now to FIGS. 13 and 14, as the rotation rod 2200 is rotated in the direction of the arrow "C", the hook portion 2150 is displaced proximally (in the direction of an arrow "P"), such that the active lead 850 is received in the groove 2152 of the hook portion 2150 and stretches the active lead 850 defining a loop. In this manner, the clinician may selectively adjust the tension in the active lead 850. Once the desired tension is achieved in the active lead 850, the locking clip 2300 is placed in the cutout 817 of the base portion 810 such that the locking clip 2300 inhibits rotation of the rotation rod 2200, e.g., in the direction opposite of the arrow "C", thereby maintaining the desired tension in the active lead 850.

Figure 15:
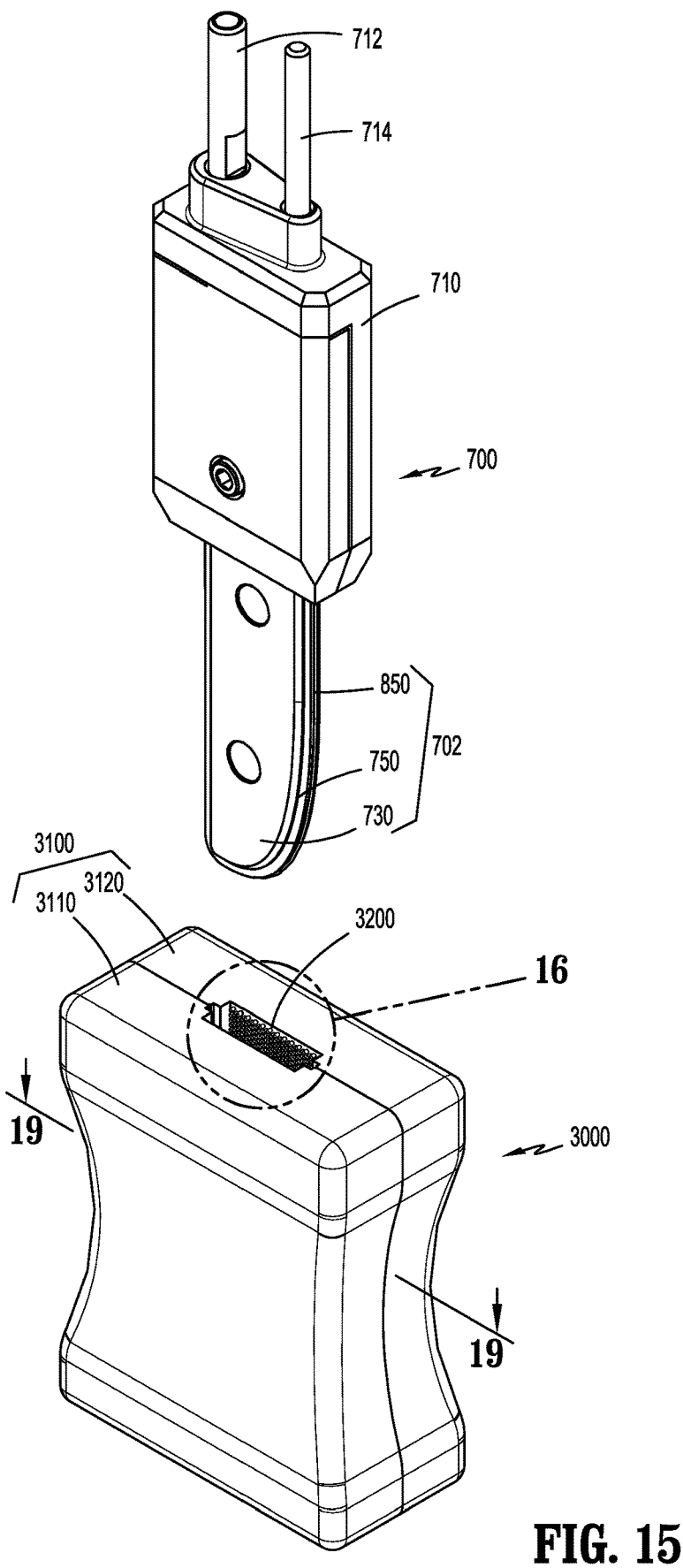
FIG. 15 is a perspective view of a tool system for use with an electrosurgical device in accordance with an aspect of the present disclosure.

With reference now to FIG. 15, there is provided a cleaning assembly 3000 configured to clean end effector assemblies 100, 700, 800 for use with an electrosurgical device in accordance with another aspect of the present disclosure. The cleaning assembly 3000 is configured to remove, e.g., tissue or eschar, off of the tool assemblies 100, 700, 800 without damaging the fragile active leads 300, 850 in the form of a wire. While the cleaning assembly 3000 is configured for use with the end effector assemblies described hereinabove, in the interest of brevity, the cleaning assembly 3000 is described with the end effector assembly 700. Portions of the end effector assembly 700 substantially similar to the portion of the end effector assemblies 100, 800 described hereinabove will not be described herein to avoid obscuring the present disclosure in unnecessary detail. The end effector assembly 700 is adapted to be coupled (releasably or integrally) to the body portion 10 (reference FIG. 2), e.g., a handpiece, of an electrosurgical device to cut tissue. The end effector assembly 700 includes a tool portion 702 and a base portion 710 supporting the tool portion 702. The tool portion 702 includes the active lead 850 electrically coupled to the electrosurgical energy source (e.g., via an active terminal), an electrical insulator 750 supporting the active lead 850 in a peripheral groove of the electrical insulator 750, and a return lead 730 electrically coupled to the electrosurgical energy source (e.g., via a return terminal) and disposed on opposing surfaces of the electrical insulator 750 in a superposed relation. The base portion 710 supports the electrical insulator 750, the return lead 730, and a tensioning mechanism (not shown). The return lead 730 serves as an electrical return for electrosurgical energy (e.g., electric current) conducted through the active lead 850. The active lead 850 may be formed of a conductive material such, e.g., as tungsten.

The base portion 710 may be formed of or coated with an electrically-insulative material. The base portion 710 includes a supply line 712, e.g., an electrical contact pin, electrically coupling the active lead 850 to the active terminal of the electrosurgical energy source, and a return line 714, e.g., an electrical contact pin, electrically coupling the return lead 730 to the return terminal of the electrosurgical energy source. The electrical insulator 750 extends through a slot of the base portion 710 and supports the active lead 850 on the peripheral portion of the electrical insulator 750. In particular, the peripheral portion defines a groove configured to receive the active lead 850 therein. For example, the electrical insulator 750 may be formed of a ceramic material due to its hardness and inherent ability to withstand high temperature fluctuations. Alternatively, the electrical insulator 750 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Activation of the electrosurgical device draws the electrosurgical energy from the electrosurgical energy source to the active lead 850. For example, the return lead 730 is configured to contact tissue at approximately the same time as the active lead 850, and thus performing a cut in tissue. The return lead 730 returns the electrosurgical energy to the electrosurgical energy source via the return terminal of the electrosurgical energy source. Under such a configuration, the electrosurgical energy applied via the active lead 850 across tissue severs tissue. The use and operation of the end effector assembly 700 are otherwise substantially similar to the use and operation of the tool assemblies described hereinabove, and thus will not be described herein.

The cleaning assembly 3000 includes a housing 3100 having first and second housing halves 3110, 3120. The cleaning assembly 3000 defines a slot 3200 dimensioned to receive the tool portion 702 of the tool assembly 700.

Figure 16:
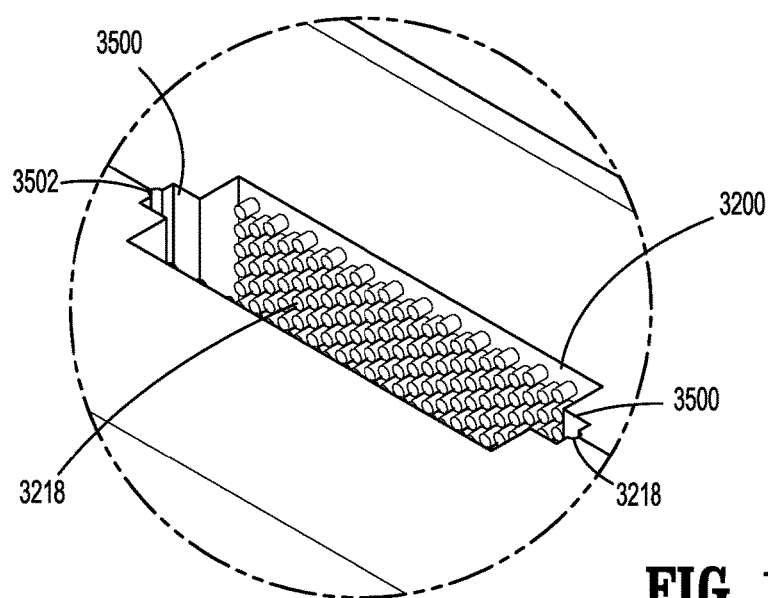
FIG. 16 is an enlarged perspective view of the indicated area of detail of FIG. 15.
Figure 17:
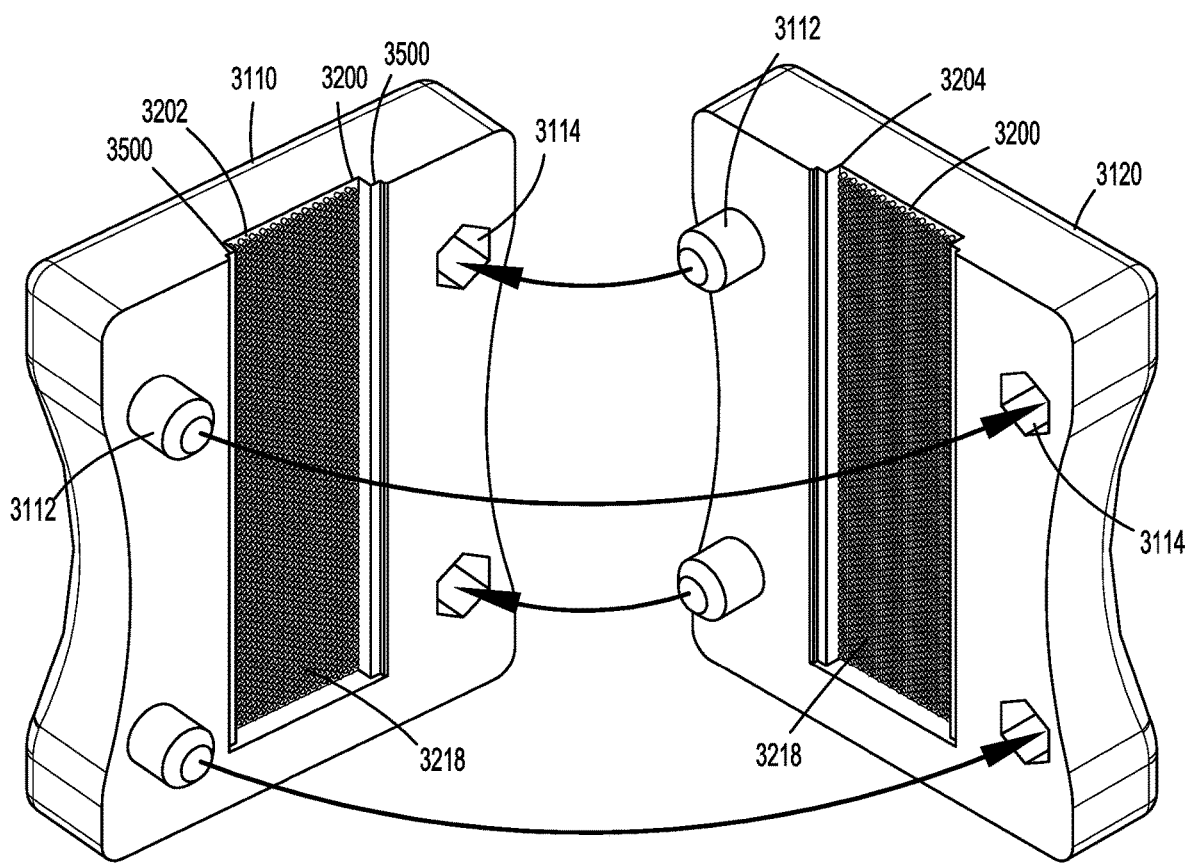
FIG. 17 is a perspective view of a cleaning assembly of FIG. 15 with first and second housing halves separated.
Figure 18:
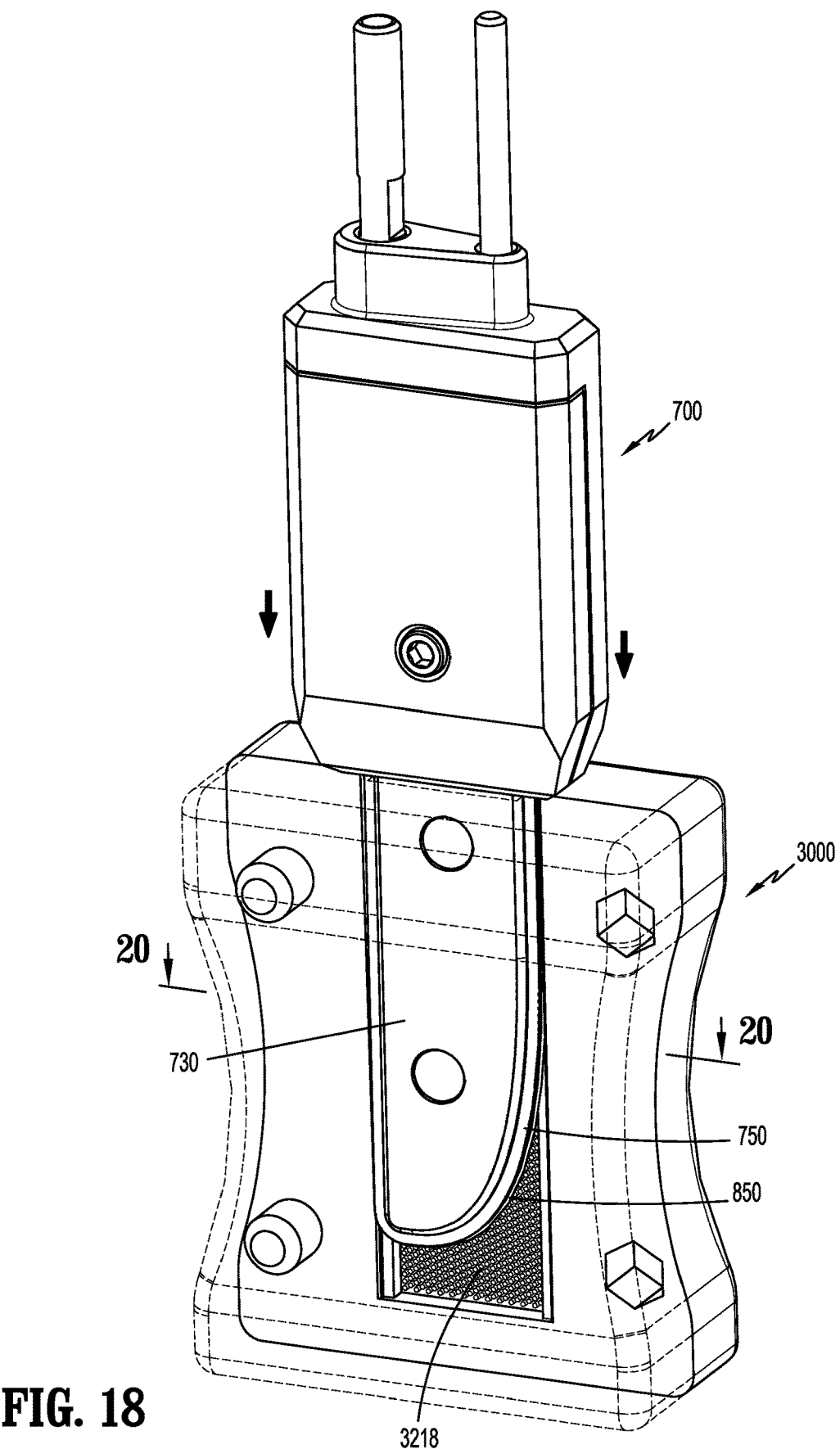
FIG. 18 is a perspective view of the cleaning system of FIG. 15, illustrating use thereof.

With reference to FIGS. 16 and 17, the first and second housing halves 3110, 3120 include bosses 3112 and corresponding bores 3114 configured to detachably secure the bosses 3112 therein by, e.g., friction fit, snap fit, etc. Alternatively, the first and second housing halves 3110, 3120 may be, e.g., magnetically, coupled to each other. The slot 3200 includes a plurality of, e.g., abrasive, bristles extending from opposing walls 3202, 3204 of the respective first and second housing halves 3110, 3120. The plurality of abrasive bristles 3218 are configured to remove debris such as, e.g., tissue and eschar, from surfaces of the return lead 730 and/or electrical insulator 730.

With particular reference to FIG. 16, the cleaning assembly 3000 further defines lateral grooves 3500 on opposing sides of the slot 3200. In particular, the lateral grooves 3500 are in communication with the slot 3200. Under such a configuration, the lateral grooves 3500 are configured to receive portions of the electrical insulator 750 that are laterally outward of the return lead 730. In addition, the lateral grooves 3500 further includes arcuate portions 3502 configured to receive the active lead 850 disposed on peripheral groove of the electrical insulator 750 such that the active lead 850 are protected from the abrasive bristles 3218. Further, the lateral grooves 3500 further serve as guides when the tool portion 702 is inserted into the cleaning assembly 3000 such that the plurality of abrasive bristles 3218 engages the return lead 730 on opposing surfaces of the electrical insulator 750.

With reference to FIGS. 18-21, in use, the tool portion 702 (FIG. 15) of the end effector assembly 700 is inserted into the slot 3200 of the cleaning assembly 3000 such that the portions of the active lead 850 and the electrical insulator 750 laterally outwards of the return lead 730 are received in the lateral grooves 3500 of the cleaning assembly. In this manner, the return lead 730 on opposing sides of the electrical insulator 750 slidably engages the plurality of abrasive bristles 3218, whereby, the debris such as, e.g., tissue or eschar, may be removed from the return lead 730. In this manner, the cleaning assembly 3000 may effectively and safely remove debris from the end effector assembly 700 while protecting the active lead 850 from the abrasive bristles 3218.

It is contemplated that the end effector assemblies 100, 700, 800 may be configured to connect to a robotic arm of a robotic surgical system to enable manipulation and control thereof.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrode assembly for use with an electrosurgical instrument, comprising:
   a base portion;
   an electrical insulator spaced distally from a distal end of the base portion;
   a tensioning mechanism including a slider slidably disposed in the base portion, a rotation rod threadably coupled to the slider, and a spring proximally biasing the slider; and
   an active lead adapted to be electrically coupled to an active terminal of an electrosurgical generator, the active lead having a first end portion securely fixed to the base portion and a second end portion slidably coupled to the rotation rod of the tensioning mechanism, the active lead extending around the electrical insulator,
   wherein rotation of the rotation rod causes axial displacement of the second end portion of the active lead to tension the active lead about the electrical insulator.

2. The electrode assembly according to claim 1, wherein the rotation rod of the tensioning mechanism defines a lumen configured to receive the active lead.

3. The electrode assembly according to claim 2, wherein the lumen has a first portion having a first diameter and a second portion distal of the first portion and having a second diameter smaller than the first diameter.

4. The electrode assembly according to claim 3, wherein the second end portion of the active lead has a stop slidably received in the first portion, the stop having a diameter larger than the second diameter of the second portion of the lumen.

5. The electrode assembly according to claim 1, further comprising a groove defined on a peripheral portion of the electrical insulator, the active lead configured to be received within the groove.

6. The electrode assembly according to claim 1, wherein the base portion includes first and second insulation tubes electrically insulating the respective first and second end portions of the active lead.

7. The electrode assembly according to claim 1, wherein the active lead is a wire.

8. The electrode assembly according to claim 1, further comprising a return lead.

9. The electrode assembly according to claim 8, wherein a gap is defined between the active lead and the return lead.

10. The electrode assembly according to claim 1, wherein the electrical insulator is rotatable relative to the base portion.

11. The electrode assembly according to claim 1, wherein the base portion is electrically insulative.

12. An electrode assembly for use with an electrosurgical instrument, comprising:
- a base portion;
- an electrical insulator disposed exterior to the base portion;
- a tensioning mechanism including a slider slidably disposed in the base portion, a rotation rod threadably coupled to the slider, and a spring proximally biasing the slider; and
- an active lead adapted to be electrically coupled to an active terminal of an electrosurgical generator, the active lead having a first portion disposed within the base portion and a second portion extending around the electrical insulator, wherein the first portion of the active lead is operably coupled to the tensioning mechanism,
- wherein rotation of the rotation rod causes axial displacement of the first portion of the active lead relative to the second portion of the active lead to tension the active lead about the electrical insulator.

13. The electrode assembly according to claim 12, wherein the first portion of the active lead includes first and second opposing ends of the active lead.

14. The electrode assembly according to claim 12, further comprising a return lead extending from the base portion, wherein the electrical insulator electrically insulates the active and return leads from one another.

15. The electrode assembly according to claim 14, wherein the return lead supports the electrical insulator on a portion of the return lead.

16. The electrode assembly according to claim 12, wherein the rotation rod of the tensioning mechanism defines a lumen configured to receive the active lead.

17. The electrode assembly according to claim 16, wherein the lumen has a first portion and a second portion, and wherein the active lead has a stop slidably received in the first portion of the lumen, the stop inhibited from entering the second portion of the lumen.

18. The electrode assembly according to claim 12, wherein the electrical insulator defines a groove and wherein the active lead is configured to be at least partially received within the groove.

19. The electrode assembly according to claim 12, wherein the base portion includes at least one insulation tube disposed about the active lead.

20. The electrode assembly according to claim 12, wherein the active lead is a wire.

* * * * *